US010246506B2

(12) United States Patent
Gagnon

(10) Patent No.: US 10,246,506 B2
(45) Date of Patent: Apr. 2, 2019

(54) METHODS FOR REDUCING LEVELS OF PROTEIN-CONTAMINANT COMPLEXES AND AGGREGATES IN PROTEIN PREPARATIONS BY TREATMENT WITH ELECTROPOSITIVE ORGANIC ADDITIVES

(71) Applicant: AGENCY FOR SCIENCE, TECHNOLOGY AND RESEARCH, Connexis (SG)

(72) Inventor: Peter Gagnon, Centros (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 54 days.

(21) Appl. No.: 14/555,224

(22) Filed: Nov. 26, 2014

(65) Prior Publication Data
US 2015/0148526 A1  May 28, 2015

Related U.S. Application Data

(63) Continuation of application No. PCT/SG2013/000049, filed on Feb. 6, 2013.

(60) Provisional application No. 61/653,752, filed on May 31, 2012.

(51) Int. Cl.
| | | |
|---|---|---|
| C07K 16/00 | (2006.01) | |
| C07K 1/30 | (2006.01) | |
| C07K 1/20 | (2006.01) | |
| C07K 1/14 | (2006.01) | |

(52) U.S. Cl.
CPC ............. *C07K 16/00* (2013.01); *C07K 1/145* (2013.01); *C07K 1/20* (2013.01)

(58) Field of Classification Search
CPC .......... C07K 1/30; C07K 16/00; C07K 1/145; C07K 1/20
See application file for complete search history.

(56) References Cited

U.S. PATENT DOCUMENTS

| 5,559,250 A | 9/1996 | Cook et al. |
|---|---|---|
| 7,947,813 B2 | 5/2011 | Fahrner et al. |
| 2003/0231981 A1* | 12/2003 | Johnson .............. A61M 1/3679 422/44 |
| 2008/0193981 A1 | 8/2008 | Fahrner et al. |

FOREIGN PATENT DOCUMENTS

| CN | 102395885 A | 3/2012 |
|---|---|---|
| EP | 0 226 448 | 6/1992 |
| JP | 61-1393 | 1/1986 |
| JP | 11-501046 | 1/1999 |
| WO | WO 2009/046840 | 4/2009 |
| WO | WO 2009/149067 | 12/2009 |
| WO | 2010118861 A1 | 10/2010 |
| WO | WO2010/118861 | 10/2010 |
| WO | 2012040216 A1 | 3/2012 |
| WO | WO2012/040216 | 3/2012 |
| WO | WO 2013/180647 | 12/2013 |
| WO | WO 2013/180648 | 12/2013 |
| WO | WO 2013/180655 | 12/2013 |

OTHER PUBLICATIONS

Gagnon et al Journal of Chromatography A, 1218 (2011) 2405-2412.*
Gagnon et al. (Bioprocess International, 2006 retrieved from http://www.bio-rad.com/webroot/web/pdf/ps/literature/Bulletin_RP0033.pdf.*
Persson et al., (Biotechnology and Bioengineering, vol. 87, No. 3, Aug. 5, 2004).*
Petsch et al. (Journal of Biotechnology 76 (2000) 97-119.*
Christensen et al., "Simple separation of DNA in antibody purification", Protein expression and purification 37, (2004), pp. 468-471.
Cordes et al., Precipitation of nucleic acids with poly(ethyleneimine), Biotechnol. Prog., (1990), 6, pp. 263-285.
Dissing et al., "Integrated removal of nucleic acids and recovery of LDH from homogenate of beef heart by affinity precipitation", vol. 7, Nos. 4-5, (1998), pp. 221-229.
Gagnon et al., "Chromatographic behavior of IgM:DNA complexes", Journal of Chromatography A, 1218, (2011), pp. 2405-2412.
Gagnon, "Dissociation of antibody-contaminant complexes with hydroxyapatite", Bioprocessing Journal, vol. 9, Issue 2, Winter 2010/2011, pp. 14-24.
Glynn, "Process-scale precipitation of impurities in mammalian cell culture broth", 2009, pp. 309-324.
Kejnovsky et al., "DNA extraction by zinc", 1870-1871, Nucleic acids research, 1997, vol. 25, No. 9., 1870-1987.
Luhrs et al., "Evicting hitchhiker antigens from purified antibodies", Journal of Chromatography B 877, (2009), pp. 1543-1552.
European Search Report dated Oct. 1, 2015 for Appln. No. 13797757.5.
Gagnon et al., "Nonspecific interactions of chromatin with immunoglobulin G and protein A, and their impact on purification performance", Journal of Chromatography A, May 2014, pp. 68-78.
Hamada et al., "Effect of Additives on Protein Aggregation", Current Pharmaceutical Biotechnology, Jun. 2009, vol. 10, No. 4, pp. 400-407.

(Continued)

*Primary Examiner* — Julie Wu
*Assistant Examiner* — Carmencita M Belei
(74) *Attorney, Agent, or Firm* — Pillsbury Winthrop Shaw Pittman, LLP

(57) ABSTRACT

Methods for reduction of aggregate levels in antibody and other protein preparations through treatment with low concentrations of electropositive organic additives (e.g., ethacridine, chlorhexidine, or polyethylenimine) in combination with ureides (e.g., urea, uric acid, or allantoin) or organic modulators (e.g., nonionic organic polymers, surfactants, organic solvent or ureides). Some aspects of the invention relate to methods for reducing the level of aggregates in conjunction with clarification of cell culture harvest. It further relates to the integration of these capabilities with other purification methods to achieve the desired level of final purification.

44 Claims, No Drawings

(56) References Cited

OTHER PUBLICATIONS

Japanese Office Action dated Sep. 27, 2016 for Appln. No. 2015-514965.
Matsuzawa et al., Study on DNA precipitation with a cationic polymer PAC(poly aluminuim chloride), 2003, Nucleic acids research supplement No. 3, pp. 163-164.
Ma et al., "Using precipitation by polyamines as an alternative to chromatographic separation in antibody purification processes", Journal of Chromatography B 878, (2010), pp. 798-806.
Mechetner et al., "The effects of hitchhiker antigens co-eluting with affinity-purified research antibodies", Journal of Chromatography B 879, (2011), pp. 2583-2594.
Ongkudon et al., "Analysis of selective metal-salt-induced endotoxin precipitation in plasmid DNA purification using improved limulus amoebocyte lysate assay and central composite design", Anal. Chem. 2011, 83, pp. 391-397.
Peram et al., "Monoclonal antibody purification using cationic polyelectrolytes: an alternative to column chromatography", Botechnol. Prog., 2010, vol. 26, No. 5, pp. 1322-1331.
Shukla et al., "Host cell protein clearance during protein a chromatography: development of an improved column wash step", Biotechnol. Prog. 2008, vol. 24, No. 5, pp. 1115-1121.
Akcasu et al., "5-Hydroxytryptamine in cerebrospinal fluid", vol. 187, 1960, p. 324.
Andersson et al. "Protein stabilising effect of polyethyleneimine" Journal of Biotechnology 72, (1999) pp. 21-31.
Arakawa et al., "Solvent Modulation of Column Chromatography", Protein and Peptide Letters, Jul. 2008, vol. 15, No. 6, pp. 544-555.
Bondos et al., "Detection and prevention of protein aggregation before, during, and after purification", Analytical Biochemistry 316, (2003), pp. 223-231.
Davis et al., "Structure of human tumor necrosis factor derived from recombinant DNA", Biochemistry, vol. 26, No. 5, 1987, pp. 1322-1326.
Fink et al., "Metabolism of intermediate pyrimidine reduction products in vitro", Journal Biol. Chem., 1956, 218, pp. 1-8.
Lopez-Vara, et al., "Refolding and Characterization of Rat Liver Methionine Adenosyltransferase from *Escherichia coli* Inclusion Bodies", Protein Expression and Purification, Jul. 2000, vol. 19, No. 2, pp. 219-226.
International Search Report dated Apr. 8, 2013 for Appln. No. PCT/SG2013/000049.
English translation of Chinese Office Action dated Aug. 2, 2017, for CN Application No. 2013-80040495.4.
English translation of Japanese Office Action dated Apr. 25, 2017, for JP Application No. 2015-514965.
English translation of Chinese Office Action dated Aug. 2, 2017, for Application No. 2013-80040495.4.
English translation of Japanese Office Action dated Apr. 25, 2017 for Application No. 2015-514965.

* cited by examiner

METHODS FOR REDUCING LEVELS OF PROTEIN-CONTAMINANT COMPLEXES AND AGGREGATES IN PROTEIN PREPARATIONS BY TREATMENT WITH ELECTROPOSITIVE ORGANIC ADDITIVES

CROSS-REFERENCE TO RELATED APPLICATIONS

This application is a continuation of PCT/SG2013/000049 filed Feb. 6, 2013, which claims the priority of U.S. Provisional Application No. 61/653,752, filed May 31, 2012 the disclosures of which are incorporated herein by reference in their entireties.

FIELD OF THE INVENTION

This invention relates to methods for enhancing purification of proteins, including antibodies. It particularly relates to methods for reducing the level of aggregates, including in conjunction with clarification of cell culture harvest. It further relates to the integration of these capabilities with other purification methods to achieve the desired level of final purification.

BACKGROUND OF THE INVENTION

It has been indicated that unnatural hetero-associations form spontaneously between host cell-derived contaminants and recombinant proteins produced by in vitro cell culture methods (Shukla et al., Biotechnol. Progr. (2008) 24:1115-1121; Luhrs et al., J. Chromatogr. B (2009) 877:1543-1552; Mechetner et al., J. Chromatogr. B (2011) 879:2583-2594; Gagnon et al., J. Chromatogr. A, (2011) 1218:2405-2412; Gagnon, Bioprocessing J. (2010) 9(4):14-24). These hetero-associations may be considered unnatural in two respects: 1) constituent contaminants are often of non-human origin, secreted by living non-human host cells or released into the culture media when non-human host cells lyse upon death. In living humans, such non-human contaminants do not exist; and 2) constituent contaminants accumulate to high concentrations in comparison to human in vivo systems where dead cell constituents are quickly eliminated. Accordingly, recombinant products are exposed to high levels of strongly interactive contaminants at concentrations that typically do not occur in living systems. Meanwhile, high expression levels of recombinant proteins make them suitable substrates for non-specific associations with these non-human contaminants, favoring the formation of undesirable hetero-associations of diverse composition including complexes and aggregates.

The contaminating protein content of hetero-aggregates has been addressed to some extent via direct targeting of the contaminating protein (Shukla et al. and Gagnon et al. supra), as well as indirectly via targeting of the corresponding DNA component responsible for the contaminating protein (Luhrs et al. and Gagnon supra). A reduction of antibody aggregate level has been indicated when some complexes are dissociated (Shukla et al., Mechetner et al., and Gagnon supra). The ability of anion exchangers to reduce levels of antibody-contaminant complexes has been disclosed (Luhrs et al. and Gagnon et al., supra), but an anion exchange treatment that was able to fully eliminate hetero-aggregates has not been indicated. Size exclusion, cation exchange, and hydrophobic interaction chromatography have also been employed in attempts to reduce hetero-aggregates, but these techniques were generally inferior to anion exchange (Gagnon et al., supra).

Treating antibody preparations with agents that might be expected to dissociate hetero-aggregates has generally proven ineffective. For example, employing high concentrations of urea, salts, or combinations of the two does not substantially dissociate IgM-contaminant hetero-aggregates (Gagnon et al., supra). Protein A affinity chromatography with pre-elution washes of urea, alcohol, and surfactants has been indicated to reduce hetero-aggregate levels more effectively than without washes (Shukla et al., supra), as did pre-elution washes combining urea, salt, and EDTA with protein G affinity chromatography (Mechetner et al., supra). Anion exchange chromatography with a pre-elution wash of urea has been indicated to reduce hetero-aggregates more effectively than in the absence of a urea wash (Gagnon et al., supra). Cation exchange chromatography has also been indicated to reduce hetero-aggregates more effectively with a pre-elution EDTA wash than without the wash (Gagnon et al., supra). Finally, hydroxyapatite with pre-elution washes of urea and/or salt have also reduced hetero-aggregates more effectively than without such washes (Gagnon, supra). Despite these observations, in general, the use of dissociating agents in pre-elution washes of antibodies bound to chromatography columns has been only moderately successful.

Electropositive organic additives have been indicated for the precipitation of acidic proteins (Farhner et al., U.S. Patent Application No. 20080193981; Ma et al., J. Chromatogr. B (2010) 878:798-806; Peram et al., Biotechnol. Progr., (2010) 26:1322-1326; Glynn, in U. Gottschalk (ed.), Process Scale Purification of Antibodies, J. T. Wiley and Sons, (2009) Hoboken, 309-324), as well as for precipitation of DNA and endotoxins (Glynn supra; Cordes et al., Biotechnol. Progr., (1990) 6:283-285; Dissing et al., Bioseparation, (1999) 7 221:9-11) and inactivation of virus (Bernhardt, U.S. Pat. No. 5,559,250). Multivalent metal cations have also been indicated to remove DNA and endotoxin from some protein preparations (Akcasu et al., Nature, (1960) 187:323-324; Matsuzawa et al., Nucl. Acids Res., (2003) 3(3):163-164; Christensen et al., Prot. Expr. Purif., (2004) 37:468-471; Kejnovsky et al., Nucl. Acids Res., (1997) 25:1870-1871; Ongkudon et al., Anal. Chem., (2011) 83 391:13-17).

SUMMARY OF THE INVENTION

This invention provides in certain embodiments methods for reducing the amount of product-contaminant complexes and aggregates in a sample containing a desired protein species, such as a protein preparation, by treating the sample with electropositive organic additives. In certain embodiments, the reduction of complexes and/or aggregates is achieved with ultralow levels of electropositive organic additives. In certain embodiments, the invention particularly reduces the content of aggregates that include chromatin remnants, such as nucleosomes, and/or histones, and/or DNA. In certain embodiments, the sample is treated at elevated conductivity values (salt concentration). In certain embodiments, the sample is additionally treated with an undissolved ureide and the supernatant containing the desired protein is collected. In certain embodiments, the sample is alternatively or additionally treated with other organic additives such as a nonionic organic polymer, organic solvent, surfactant, or ureide intended to enhance dissociation of contaminants associated with the desired protein in complexes and aggregates. In certain embodiments, the treated sample is subsequently exposed to solid materials bearing chemical moieties that selectively remove electropositive organic additives and potentially other chemical entities from the desired protein.

DETAILED DESCRIPTION OF THE INVENTION

Methods and kits are provided for the purification of proteins. In certain embodiments the invention provides for the reduction of protein-contaminant complexes and aggregates from preparations of antibodies or other proteins through the contact of such desired protein with an electropositive organic additive. In certain embodiments, the invention may be practiced at a range of conductivity levels from so-called physiological conditions to conductivity values up to 3 or more times such physiological conditions; such elevated conductivity levels may suppress precipitation of the desired or target protein. In certain embodiments, the invention may be practiced with ultralow concentrations of the electropositive organic additive; such as levels 10-fold to 100-fold lower than the concentrations at which such additives are applied for the purpose of mediating precipitation. The invention provides in certain embodiments the advantages of reducing the need for method development requirements which are customized to the protein of interest, improved recovery of the protein of interest, improved reproducibility of purification methods, and reducing the need for additional process steps to remove aggregates.

Embodiments disclose herein provide methods of reducing the aggregate content of a sample comprising a desired protein, the methods comprising contacting the sample with an electropositive organic additive and an undissolved ureide.

In some such embodiments methods of reducing the aggregate content of a sample comprising a desired protein at a conductivity value of 15 mS/cm or higher, the method comprising adding an electropositive organic additive at a concentration of 0.1% or less.

In one or more of the preceding embodiments, methods of reducing the aggregate content of a sample comprising a desired protein, the sample having a conductivity value of 5 mS/cm or higher, comprising adding an electropositive organic additive at a concentration of 0.1% or less, in the presence of one or more organic additives to reduce the formation of precipitates, wherein the one or more organic additives are selected from the group consisting of a ureide, an organic solvent, or a surfactant.

In one or more of the preceding embodiments, methods of reducing the amount of aggregate content of a sample comprising a desired protein, the method comprising providing the sample containing aggregates wherein the desired protein is in solution in the sample and contacting the sample with an electropositive organic additive.

In one or more of the preceding embodiments, the ureide is allantoin.

In one or more of the preceding embodiments, the ureide is present in a range of from about 0.5% to about 2% weight/volume.

In one or more of the preceding embodiments, the electropositive organic additive comprises one selected from the group consisting of ethacridine, chlorhexidine, polyethyleneimine, methylene blue, and benzalkonium chloride.

In one or more of the preceding embodiments, the ureide is added before electropositive organic additive.

In one or more of the preceding embodiments, a salt is added to a level to substantially prevent precipitation of the desired protein.

In one or more of the preceding embodiments, the desired protein comprises one selected from the group consisting of an antibody, a Factor VIII, a growth hormone, and a recombinant protein.

In one or more of the preceding embodiments, the electropositive organic additive is added to a level of 1% or less weight/volume.

In one or more of the preceding embodiments, the electropositive organic additive is added to a level of 0.1% or less weight/volume.

In one or more of the preceding embodiments, the electropositive organic additive is added to a level of 0.01% or less weight/volume.

In one or more of the preceding embodiments, the electropositive organic additive is added to a level of 0.001% or less weight/volume.

In one or more of the preceding embodiments, the electropositive organic additive is present at a concentration ranging from 0.02% to 0.03%.

In one or more of the preceding embodiments, more than one electropositive organic additive is present.

In one or more of the preceding embodiments, the aggregate concentration of the more than one electropositive organic additive is 1% or less weight/volume.

In one or more of the preceding embodiments, the aggregate concentration of the more than one electropositive organic additive is 0.1% or less weight/volume.

In one or more of the preceding embodiments, the aggregate concentration of the more than one electropositive organic additive is 0.01% or less weight/volume.

In one or more of the preceding embodiments, the aggregate concentration of the more than one electropositive organic additive is 0.001% or less weight/volume.

In one or more of the preceding embodiments, the undissolved ureide is allantoin.

In one or more of the preceding embodiments, allantoin is present at a concentration in range of from about 0.56% weight/volume to about 1% weight/volume.

In one or more of the preceding embodiments, allantoin is present at a concentration in range of from about 1% weight/volume to about 2% weight/volume.

In one or more of the preceding embodiments, allantoin is present at a concentration in range of from about 2% weight/volume to about 5% weight/volume.

In one or more of the preceding embodiments, allantoin is present at a concentration in range of from about 5% weight/volume to about 10% weight/volume.

In one or more of the preceding embodiments, allantoin is present at a concentration in range of from about 10% weight/volume to about 15% weight/volume.

In one or more of the preceding embodiments, ureide is added to the sample before addition of the electropositive organic additive.

In one or more of the preceding embodiments, the conductivity of the sample is adjusted to a sufficiently high level to counteract substantial loss of the desired protein through precipitation.

In one or more of the preceding embodiments, the conductivity of the sample is adjusted to a level that is higher than necessary to counteract substantial loss of the desired protein.

In one or more of the preceding embodiments, the conductivity of the sample is adjusted up to twice physiological conductivity.

In one or more of the preceding embodiments, the conductivity of the sample is adjusted up to thrice physiological conductivity, or more.

In one or more of the preceding embodiments, the conductivity of the sample is reduced but remains high enough to counteract substantial loss of the desired proteins.

In one or more of the preceding embodiments, the conductivity of the sample is adjusted before addition of the electropositive organic additive.

In one or more of the preceding embodiments, an organic solvent is present.

In one or more of the preceding embodiments, the organic solvent comprises one selected from the group consisting of ethanol, isopropanol, ethylene glycol, propylene glycol, tri(n-butyl)phosphate, and glycerol.

In one or more of the preceding embodiments, the organic solvent comprises a concentration in a range of from about 0.01% to about 20% weight/volume.

In one or more of the preceding embodiments, the organic solvent comprises ethylene glycol, propylene glycol, glycerol, ethanol, isopropanol, or tri(n-butyl)phosphate at a concentration in range of from about 0.01 to about 1%.

In one or more of the preceding embodiments, the organic solvent comprises ethylene glycol, propylene glycol, glycerol, ethanol, or isopropanol at a concentration in range of from about 1% to about 5%.

In one or more of the preceding embodiments, the organic solvent comprises ethylene glycol, propylene glycol, glycerol, ethanol, or isopropanol at a concentration in range of from about 5% to about 10%.

In one or more of the preceding embodiments, the organic solvent comprises ethylene glycol, propylene glycol, or glycerol at a concentration in range of from about 10% to about 20%.

In one or more of the preceding embodiments, an organic solvent is present and comprises one selected from the group consisting ethanol, isopropanol, and tri(n-butyl)phosphate.

In one or more of the preceding embodiments, the organic solvent concentration is less than 1%.

In one or more of the preceding embodiments, the organic solvent concentration is less than 0.1%.

In one or more of the preceding embodiments, the organic solvent concentration is less than 0.01%.

In one or more of the preceding embodiments, a soluble ureide is present.

In one or more of the preceding embodiments, the soluble ureide is urea.

In one or more of the preceding embodiments, the soluble ureide is present at a concentration in a range of from about 0.5 M to about 1 M.

In one or more of the preceding embodiments, the soluble ureide is present at a concentration in a range of from about 1 M to about 2 M.

In one or more of the preceding embodiments, the soluble ureide is present at a concentration in a range of from about 2 M to about 4 M.

In one or more of the preceding embodiments, the soluble ureide is present at a concentration in a range of from about 4 M to about 8 M.

In one or more of the preceding embodiments, a surfactant is present.

In one or more of the preceding embodiments, the surfactant comprises a nonionic surfactant.

In one or more of the preceding embodiments, the nonionic surfactant comprises one selected from the group consisting of Tween and Triton.

In one or more of the preceding embodiments, the surfactant comprises a zwitterionic surfactant.

In one or more of the preceding embodiments, the zwitterionic surfactant comprises one selected from the group consisting of CHAPS, CHAPSO, and octaglucoside.

56. The method of any one of claims 51 to 55, wherein the surfactant is present at a non-zero concentration less than 1%.

In one or more of the preceding embodiments, the surfactant is present at a non-zero concentration less than 0.1%.

In one or more of the preceding embodiments, the surfactant is present at a non-zero concentration less than 0.01%.

In one or more of the preceding embodiments, a chelating agent is present.

In one or more of the preceding embodiments, the chelating agent is positively charged.

In one or more of the preceding embodiments, the positively charged chelating agent comprises tris(2-aminoethyl)amine or deferoxamine.

In one or more of the preceding embodiments, the chelating agent is present at a non-zero concentration of less than 100 mM.

In one or more of the preceding embodiments, the chelating agent is present at a non-zero concentration of less than 50 mM.

In one or more of the preceding embodiments, the chelating agent is present at a non-zero concentration of less than 20 mM.

In one or more of the preceding embodiments, the chelating agent is present at a non-zero concentration of less than 10 mM.

In one or more of the preceding embodiments, the chelating agent is present at a non-zero concentration of less than 5 mM.

In one or more of the preceding embodiments, more than one of the following is present: (a) an organic solvent, (b) an organic polymer, (c) a soluble ureide, (d) a surfactant, (e) a chelating agent, and (f) a salt.

In one or more of the preceding embodiments, the contacted sample is exposed to one or more solids to remove at least one electropositive organic additive before subsequent processing steps to fractionate the desired protein from remaining contaminants.

A kit may be provided for practicing the methods of any one of preceding embodiments.

In certain embodiments, the invention provides methods for reducing levels of aggregates which have high molecular weight in comparison with the desired protein, such as homo-aggregates, and also for reducing levels of aggregates of hydrodynamic size only modestly greater than the desired protein, such as hetero-aggregates. In certain embodiments, aggregates comprise hetero-aggregates of the desired protein and a contaminant and in certain such embodiments the contaminant is a nucleic acid, nucleotide, endotoxin, metal ion, protein, lipid, or cell culture media component. In certain embodiments, the presence of homo-aggregates of the desired protein is substantially eliminated. In certain embodiments, the presence of hetero-aggregates of the desired protein and a contaminant is substantially eliminated.

In certain embodiments, the invention additionally provides for the reduction of contaminants such as DNA, endotoxin, and virus levels along with reduction of aggregates. In certain embodiments the invention is practiced with the additional inclusion of antiviral agents.

In certain embodiments, the protein species of interest (e.g., the desired protein to be purified) is of recombinant origin, and the protein preparation may include a cell-containing cell culture harvest, a cell culture supernatant, clarified cell culture supernatant, an eluate from a chromatography column, or protein-containing solution obtained from a previous stage of purification. In certain embodiments, the protein preparation contains an antibody and in certain of such embodiments the antibody is an IgG, an IgM, or a fragmentary form thereof, or a fusion protein of an antibody or antibody fragment, such as an Fc-fusion protein. In certain embodiments, the desired protein may be a clotting protein, such as Factor VIII. In certain embodiments, the desired protein may be a peptide hormone, such as human growth hormone.

In certain embodiments, the invention is practiced such that the conductivity of the sample is at a sufficiently high level to substantially avoid precipitation of the desired protein from the sample. Conductivity may be adjusted by addition of salts or diluents according to methods known in the art. In certain embodiments, the conductivity is 5 mS/cm, 10 mS/cm, 15 mS/cm or 20 mS/cm greater than the level determined to be needed to avoid substantial precipitation of the desired protein. In certain embodiments, the conductivity is greater than 20 mS/cm, 25 mS/cm, 30 mS/cm, 35 mS/cm, 40 mS/cm, 45 ms/cm or greater than 45 mS/cm. The ability of the method to remove important subsets of contaminants at elevated conductivities represents one of the surprising features of the invention, since charge interactions in these system are known to be reduced at elevated conductivities. At conductivities of 25 mS/cm and higher for example, only a minority of negatively charged proteins are known to bind to electropositive surfaces. Apart from the present method, application of most electropositive agents to preparations of IgG antibodies occurs at conductivities less than 5 mS/cm, and usually with the additional operating requirement of alkaline pH. Such an operating pH is not a requirement of the present method. It will be apparent to the person of ordinary skill in the art that elevated conductivity may have the effect of weakening internal electrostatic associations within aggregates and thereby increase the ability of the method to achieve dissociation of aggregates and/or removal of contaminants associated with the desired protein.

In certain embodiments, the electropositive organic additive is ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), polyethyleneimine (Poly(iminoethylene)), chlorhexidine, or a poly-amino acids. In certain embodiments, the electropositive organic additive is ethacridine, polyethylenimine or chlorhexidine or a salt thereof.

In certain embodiments, the electropositive organic additive is provided at substantially the lowest concentration sufficient to promote the desired degree of reduction of aggregates. In certain embodiments, the concentration of the electropositive organic additive may be less than (on a weight per volume basis) 0.1%, 0.05%, 0.04%, 0.025%, or 0.001%. In certain embodiments the electropositive organic additive is provided in concentrations of 0.01-0.04% or 0.02-0.025%. In certain of such embodiments the electropositive organic additive is ethacridine, polyethyleneimine (PEI), or chlorhexidine. The ability of the method to achieve a useful effect where the concentration of the electropositive organic additive is less than 0.1% highlights another one of the surprising features of the method: in addition to operating at elevated conductivity and without requirement for alkaline pH, the method can be highly effective without causing formation of a significant amount of precipitation. Electropositive organic additives are commonly used to mediate precipitation of acidic proteins, DNA, and virus, among other contaminants. They are accordingly used at high concentration such as 1% or more. The objective of the present method is to dissociate aggregates, or weaken internal associations within aggregates, or remove non-product contaminants that stabilize aggregates. In many embodiments, it is a secondary objective of the method to minimize or avoid precipitation to minimize or avoid the need for their removal, which is a reason for both the low concentration of electropositive organic additives and the high operating conductivities.

In certain embodiments, the invention may be practiced at pH levels chosen to avoid or limit precipitation of the desired protein while reducing the amount of aggregates in the sample. The pH level may be adjusted by conventional means and may be chosen in conjunction with the selection of the conductivity. In certain embodiments, the pH of the sample is between approximately 4 and approximately 9, between approximately 5 and approximately 8, or between approximately 6 and approximately 7.5. This again highlights the unusual nature of this use of electropositive organic additives.

In certain embodiments, the sample is additionally contacted with an antiviral agent, preferably at substantially the same time as the electropositive organic additive. In certain of such embodiments, the antiviral agent itself is an electropositive organic molecule, such as a benzalkonium chloride or methylene blue. Electroneutral or nonionic antiviral agents may also be used, such as tri(n-butyl)phosphate. Antiviral agents may be present in an amount less than approximately 1% (w/v), less than approximately 0.1% (w/v), or less than approximately 0.01% (w/v) or less than approximately 0.001%. Such agents may be especially useful with proteins that do not tolerate virus inactivation by treatment at low pH.

In certain embodiments, the method additionally includes the step of contacting the sample with a ureide in an amount sufficient for the ureide to be undissolved in the sample. The supernatant containing the desired protein can then be separated from the balance of the sample including precipitated contaminants. In certain of such embodiments the ureide is supplied prior to the step of contacting the sample with the electropositive organic additive, in others the ureide is supplied substantially simultaneously with the step of contacting the sample with the electropositive organic additive, and in yet others the ureide is supplied after the step of contacting the sample with the electropositive organic additive. In certain such embodiments, the ureide can be any of uric acid, hydantoin (imidazolidine-2,4-dione), allantoin (2,5-Dioxo-4-imidazolidinyl) urea, alcloxa, aldioxa, hemocane, ureidohydantoin, 5-ureidohydantoin), glyoxylureide, glyoxylic acid diureide, 2,5-dioxo-4-imidazolidinyl urea, imidazolydinyl urea, and a purine. In certain embodiments the ureide is allantoin and in some such cases the allantoin is present in concentrations greater than 0.56% (w/v), 1%, 1.5%, 2%, or greater. In certain embodiments the ureide is uric acid and in some such cases the uric acid is present in concentrations greater than 0.0025% (w/v), 0.005%, 0.01%, 0.05%, 0.1%, 1% or greater.

In certain embodiments, the method additionally includes the step of contacting the sample with a ureide in an amount where the ureide is fully dissolved. In certain such embodiments, the soluble ureide can be urea, imidazolydinal urea, or another ureide. In certain embodiments the ureide is urea and in some such cases the urea is present in concentrations greater than 0.5 M, or greater than 1 M, or greater than 2 M, or greater than 4 M, or than 6M, or greater than 8 M. This emphasizes again the surprising nature of the method, where avoidance of protein precipitation is a particular object of the method. Highly soluble ureides such as urea have the general effect of increasing the solubility of many compounds, which is to say its presence opposes the formation of precipitates. It will be apparent to the person of ordinary skill in the art that the presence of a highly soluble ureide may have the effect of weakening internal hydrophobic and/or hydrogen bonding associations within aggregates and thereby increase the ability of the method to achieve dissociation of aggregates and/or removal of contaminants associated with the desired protein.

In certain embodiments, the utility of the invention is enhanced by the fact that it also accelerates sedimentation of cell debris in cell culture harvests, and substantially reduces levels of DNA, endotoxin, and virus, when present. Experimental data suggest that the ability of some ureides to preferentially interact with aggregates, endotoxin, and virus contribute to these results, and that low levels of dissolved ureides may contribute to the higher antibody recovery they support in comparison to treatment with electropositive organic additives in the absence of ureides. The invention is compatible with the addition of non-electropositive antiviral agents, which may further extend its utility. Following treatment, solid materials may be removed by sedimentation or filtration, leaving the substantially aggregate-free protein in the supernatant. This provides another advantage of the invention, which is that treated materials are optically clear and devoid of particulates, whereas materials treated by other methods are typically turbid and murky.

In certain embodiments, the invention may be practiced with the additional step of contacting the sample with a soluble organic modulator such as a nonionic organic polymer, organic solvent, surfactant, or ureide. In certain of such embodiments the step of contacting the sample with the organic modulator occurs prior to the step of contacting the sample with the electropositive organic additive. In others, the step of contacting the sample with the organic modulator occurs substantially simultaneously with the step of contacting the sample with the electropositive organic additive. In yet others, the step of contacting the sample with the organic modulator occurs after the step of contacting the sample with the electropositive organic additive. In certain embodiments, the organic modulator is a nonionic organic polymer such as polyethylene glycol, polypropylene glycol and polybutylene glycol and in certain of such embodiments the nonionic organic polymer has an average molecular weight of approximately 1000 D or less, 500 D or less, 250 D or less, or 100 D or less. In certain embodiments, the organic modulator is an organic solvent such as ethylene glycol, propylene glycol, butylene glycol, dimethylsulfoxide, ethanol, or phenoxyethanol. In certain embodiments, the organic modulator is provided at a concentration of approximately 1% (w/v) or greater. In certain embodiments, the organic modulator is a surfactant such as Tween, triton, CHAPS, CHAPSO or octyl glucoside and in certain of such embodiments the surfactant is provided at a concentration of approximately 1% (w/v) or less, approximately 0.1% or less or approximately 0.02% (w/v) or less. In certain embodiments, the organic modulator is a ureide provided in a subsaturating amount and in certain of such embodiments the ureide is urea, hydantoin, or allantoin. This again highlights the unusual nature of the method, where electropositive organic additives are used under conditions that reduce or eliminate the formation of significant amounts of precipitates. In addition to the unusually low concentration of the electropositive organic additives, the high operating conductivity, independence from alkaline pH, and the well-known solubilizing influence of urea, the presence of organic solvents and surfactants has the effect of weakening hydrophobic interactions between certain preferred electropositive organic additives with proteins or other contaminants. This applies especially to hydrophobic electropositive organic additives such as ethacridine or its analogues, or to chlorhexidine or benzalkonium chloride. It will be apparent to the person of ordinary skill in the art that the presence of organic additives such as those noted may have the effect of weakening internal chemical associations within aggregates and thereby increase the ability of the method to achieve dissociation of aggregates and/or removal of contaminants associated with the desired protein.

In certain embodiments, the invention provides methods for reducing the amount of aggregate content of a sample containing a desired protein in solution where the sample is contacted with an electropositive organic additive. In certain such embodiments, the conductivity of the sample is at a sufficiently high level to substantially avoid precipitation of the desired protein from the sample. In certain embodiments, the conductivity is greater than 15 mS/cm or the conductivity is greater than 30 mS/cm.

In certain embodiments, the invention provides methods where the concentration of the electropositive organic additive is less than approximately 0.1% (w/v). In certain embodiments, the electropositive organic additive is selected from the group consisting of ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), polyethyleneimine, chlorhexidine, and poly-amino acids. In certain embodiments, the invention provides methods wherein the electropositive organic additive is ethacridine, polyethylenimine or chlorhexidine or a salt thereof. In certain embodiments, the invention provides methods wherein the electropositive organic additive is present in an amount between approximately 0.01% and approximately 0.05% or in an amount less than approximately 0.01% or in an amount less than approximately 0.005% or in an amount less than approximately 0.001%.

In certain embodiments, the invention provides methods where the pH of the sample is between approximately 4 and approximately 9 or between approximately 5 and approximately 8 or between approximately 6 and approximately 7.5.

In certain embodiments, the invention provides methods the aggregates reduced include comprise homo-aggregates of the desired protein, in others the aggregates reduced include hetero-aggregates of the desired protein and a contaminant, and in others the aggregates contain both such homo-aggregates and hetero-aggregates. In certain embodiments, the invention provides methods where the aggregates are substantially eliminated in the sample. In certain embodiments, the aggregates reduced are of substantially the same hydrodynamic size as the desired protein. In certain embodiments, the aggregates reduced are heteroaggregates including a nucleic acid, nucleotide, endotoxin, metal ion, protein, lipid, or cell culture media component.

In certain embodiments, the invention provides methods where the desired protein is an antibody or antibody fragment. In certain embodiments, the sample is a cell culture harvest, a cell culture supernatant, an antibody-containing solution derived from a cell culture, or an antibody-containing solution from a previous stage of protein purification.

In certain embodiments, the invention provides methods where the sample is a desired protein containing solution from a previous stage of protein purification. In certain embodiments, the sample is an eluate from a chromatography column.

In certain embodiments, the invention provides methods where the sample is additionally contacted with an antiviral agent. In certain embodiments, the antiviral agent is selected from the group consisting of benzalkonium chloride, methylene blue and tri (n-butyl) phosphate. In certain embodiments, the antiviral agent is present in an amount less than approximately 1% (w/v) or in an amount less than approximately 0.1% (w/v) or in an amount less than approximately 0.01% (w/v).

In certain embodiments, the invention provides methods comprising the additional steps of contacting the sample with a ureide in an amount sufficient for the ureide to be undissolved in the sample, and separating the supernatant containing the desired protein from the portion of the sample.

In certain embodiments, the invention provides methods wherein the step of contacting the sample with the ureide occurs prior to the step of contacting the sample with the electropositive organic additive.

In certain embodiments, the invention provides methods wherein the step of contacting the sample with the ureide occurs substantially simultaneously with the step of contacting the sample with the electropositive organic additive.

In certain embodiments, the invention provides methods wherein the step of contacting the sample with the ureide occurs after the step of contacting the sample with the electropositive organic additive.

In certain embodiments, the invention provides methods wherein the ureide is selected from the group consisting of urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, and purines.

In certain embodiments, the invention provides methods wherein the ureide is allantoin. In certain embodiments, the invention provides methods wherein the allantoin is present in an amount greater than 0.5% (w/v). In certain embodiments, the invention provides methods wherein the allantoin is present in an amount greater than approximately 1% (w/v).

In certain embodiments, the invention provides methods wherein the ureide is uric acid. In certain embodiments, the invention provides methods wherein the uric acid is present in an amount greater than 0.0025% (w/v). In certain embodiments, the invention provides methods wherein the uric acid is present in an amount greater than approximately 0.01% (w/v). In certain embodiments, the invention provides methods wherein the uric acid is present in an amount greater than approximately 0.1% (w/v). In certain embodiments, the invention provides methods the uric acid is present in an amount greater than approximately 1% (w/v).

In certain embodiments, the invention provides methods wherein the method comprises an additional step of contacting the sample with an organic modulator selected from the group consisting of nonionic organic polymers, organic solvents, surfactants, and ureide. In certain embodiments, the invention provides methods wherein the step of contacting the sample with the organic modulator occurs prior to the step of contacting the sample with the electropositive organic additive. In certain embodiments, the invention provides methods wherein the step of contacting the sample with the organic modulator occurs substantially simultaneously with the step of contacting the sample with the electropositive organic additive. In certain embodiments, the invention provides methods wherein the step of contacting the sample with the organic modulator occurs after the step of contacting the sample with the electropositive organic additive.

In certain embodiments, the invention provides methods wherein the organic modulator is a nonionic organic polymer selected from the group consisting of polyethylene glycol, polypropylene glycol and polybutylene glycol. In certain embodiments, the invention provides methods wherein the nonionic organic polymer has an average molecular weight of approximately 500 D or less.

In certain embodiments, the invention provides methods wherein the organic modulator is an organic solvent selected from the group consisting of ethylene glycol, propylene glycol, butylene glycol, dimethylsulfoxide, ethanol, and phenoxyethanol. In certain embodiments, the invention provides methods wherein the organic modulator is provided at a concentration of approximately 1% (w/v) or greater.

In certain embodiments, the invention provides methods wherein the organic modulator is a surfactant selected from the group consisting of Tween, triton, CHAPS, CHAPSO and octyl glucoside. In certain embodiments, the invention provides methods wherein the surfactant is provided at a concentration of approximately 1% (w/v) or less. In certain embodiments, the invention provides methods wherein the surfactant is provided at a concentration of approximately 0.1% (w/v) or less. In certain embodiments, the invention provides methods wherein the organic modulator is a ureide provided in a subsaturating amount. In certain embodiments, the invention provides methods wherein the ureide is selected from the group consisting of urea, hydantoin, and allantoin.

In certain embodiments, the invention provides kits providing for the convenient practice of a method of any of the methods disclosed herein, the kit comprising an electropositive organic additive and at least one ureide in an amount sufficient for supersaturating the sample, an organic modulator, and an antiviral agent wherein the provided materials are provided in quantities sufficient for the convenient practice of the invention with respect to a sample for which the kit is provided.

In certain embodiments, the invention provides a kit for the convenient practice of certain methods of the invention. Such kit may provide reagents useful for the practice of the invention such one or more of multivalent organic cations, ureides, organic modulators, antiviral agents, and reagents for the adjustment of conductivity. The kit may provide materials in amounts and concentrations adapted to the practice of the invention for use in the purification of proteins. Such kits may be adapted for use with certain proteins such as IgG or IgM antibodies and may be adapted to quantities suitable for certain scales of protein preparation and purification. Materials may be supplied in ready to use solution form, in concentrated solutions suitable for dilution or in solid form to be used by the user in preparing solutions for use in practicing methods of the invention.

In certain embodiments, the invention may be followed by contact of the sample with solid materials with the intent of the solids having the effect of selectively removing the electropositive agents or other sample components from the sample prior to additional processing.

In certain embodiments, the invention may be combined with conventional protein purification methods to achieve higher levels of purification or to remove other contaminants. For example, the invention may be practiced in conjunction with conventional purification methods involving precipitation, chromatography, and liquid-liquid extraction methods. Such additional methods may be combined with the invention such that they are performed before during or after aspects of the invention. It is within the ability of a person of ordinary skill in the art to develop appropriate conditions for these methods and integrate them with the invention described herein to achieve the desired purification of a product.

In certain embodiments, the invention permits reduction of aggregate levels before chromatographic purification begins, removing the burden from subsequent process steps. DNA, endotoxin, and virus levels may be reduced in parallel with aggregate reduction which may further reduce the burden on downstream purification steps. In certain embodiments, the use of organic modulators in combination with low concentrations of electropositive organic additives prevents formation of substantial precipitates and potentially enables direct application of the sample treated according to the invention to a chromatography column without an intermediate process step to remove solids. Such embodiments can additionally be compatible with the addition of non-electropositive organic additive antiviral agents.

In certain embodiments, operating conditions may be varied with respect to pH, and/or by the presence of chelating agents, organic polymers or solvents, surfactants, chaotropes, and various species of salts in order to modulate the degree to which aggregates are reduced and the desired protein remains in solution.

Additional objects and advantages of the invention will be set forth in part in the description which follows, and in part will be obvious from the description, or may be learned by practice of the invention. The objects and advantages of the invention will be realized and attained by means of the elements and combinations specified in the claims.

It is to be understood that both the foregoing general description and the following detailed description are exemplary and explanatory only and are not restrictive of the invention, as claimed.

Definitions

Terms are defined so that the invention may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homoaggregates" refers to a stable association of two or more antibody molecules; "Hetero-aggregates" refers to a stable association of one or more antibody molecules with one or more non-antibody molecules. The non-antibody component may consist of one more entities from the group consisting of a nucleotide, an endotoxin, a metal ion, a protein, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

"Endotoxin" refers to a toxic heat-stable lipopolysaccharide substance present in the outer membrane of gram-negative bacteria that is released from the cell upon lysis.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the invention include but are not limited to polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 1000 daltons.

"Electropositive organic additive" refers to an organic molecule, cation or salt of natural or synthetic origin that bears at least one positive charge and may contain multiple positive charges. The electropositive organic additive may also bear negative charges but in such cases will still retain a net positive charge at under the operating conditions where it is employed. Where the electropositive organic additive is net positive it may be provided together with counterions (anions) such as chlorides, bromides, sulfates, organic acids, lactactes, gluconates, and any other anion not incompatible with the method. In certain embodiments certain of the positive charges of the electropositive organic additives are supplied by amine, imine or other nitrogen moieties. The electropositive organic additive may additionally include hydrophobic residues, metal affinity residues, hydrogen bonding residues, other functional moieties, and/or it may possess the ability to participate in other types of chemical interactions. Examples of electropositive organic additives in certain embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinyibenzyltrimethylammonia; polyvinylguanidine; poly(N-ethyl-4-vinylpyridine: DEAE-dextran; DEAE-cellulose; ethacridine (CAS number 442-16-0; 7-ethoxyacridine-3,9-diamine); tris(2-aminoethyl) amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1[(6-chloro-2-methoxy-9-acridinyl)amino]-3-(diethylamino)-2-propanol dihydrochloride), phenosafranin, phenoxazine, phenothiazine, acriflavine (3,6-diamino-10- methylacridinium, chloride and 3,6-acridineidiamine), and salts thereof (e.g. chlorides, bromides, sulfates, lactates, gluconates.)

"Organic solvent" refers to naturally occurring or synthetic organic compound existing in a liquid state. Examples suitable to practice the invention include but are not limited to ethylene glycol, propylene glycol, dimethyl sulfoxide, ethanol, and phenoxyethanol.

"Organic polymer" refers to a naturally occurring synthetic polymer of an organic monomer. Examples include but are not limited to polyethylene glycol, polypropylene glycol, dextran, or cellulose, among others.

"Polynucleotide" refers to a biopolymer composed of multiple nucleotide monomers covalently bonded in a chain. DNA (deoxyribonucleic acid) and RNA (ribonucleic acid) are examples of polynucleotides.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Undissolved ureide" refers to a solution containing an amount of ureide in excess of its maximum solubility under the conditions prevailing in a particular protein preparation. In certain embodiments, the invention provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the invention include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In preparation for using the invention according to certain embodiments, it will be necessary to select an electropositive organic additive. Experimental data reveal that as a general matter, the less hydrophobic the electropositive organic additive, the higher the recovery of the protein of interest. Also, the less hydrophobic, the wider and higher the concentration range over which the electropositive organic additive can be applied to achieve effective aggregate reduction without significant loss of protein. Thus weakly hydrophobic PEI may be considered a better candidate than the more hydrophobic ethacridine, or the much more hydrophobic chlorhexidine. However, other issues must also be taken into consideration that may transcend product recovery. PEI embodies well-known cytotoxic properties, and it is difficult to detect with adequate sensitivity to easily validate its removal from a protein preparation through the course of a purification process. Ethacridine may be preferred because of its long history in the field of plasma protein fractionation and as an antiviral agent. In addition, its bright yellow color and intrinsic fluorescence facilitate sensitive measurement of its content in a given sample, thereby aiding documentation of its removal subsequent to practicing the method. Different electropositive organic additives may embody different secondary chemical functionalities that bear on their ability to mediate the desired effect. PEI for example is understood to bind DNA chiefly through electrostatic interactions and hydrogen bonding. Ethacridine offers fewer opportunities for both interactions but is known to intercalate DNA. Such differences may contribute to subtle but useful differences in the relative suitability of one electropositive organic additive over another, which highlights the point that there may be a practical benefit to evaluating candidates that might superficially seem non-ideal.

In the course of evaluation of electropositive organic additive for use in certain embodiments, the conditions for application of the electropositive organic additive may be investigated as follows. The use of electropositive organic additive potentially imposes some restrictions on the conditions that may be used to practice the method in certain embodiments. For example, it can be desirable to employ conditions that substantially prevent strong interactions between the electropositive organic additive and the protein of interest. A simple method to obtain an approximation of such conditions is to apply the protein of interest to an anion exchanger and elute it in a salt gradient. A salt concentration just above the threshold at which the protein elutes roughly identifies the minimum conductivity at which the method may be most effectively practiced. This concentration will be influenced by pH, which can be modeled by the same means. Given that the method is applied to a cell culture supernatant, an IgG antibody may not require the addition of salt or modification of pH to avoid significant losses. IgM antibodies may require the addition of salt, even to conductivity values approaching 30 mS/cm (about 2 times higher than physiological). In certain embodiments involving the use of undissolved ureides and electropositive organic additives, IgG applications may be conducted at lower than physiological conductivity, potentially including values of 1 mS/cm or less, in which case substantial amounts of host proteins may be removed in conjunction with dissociating aggregates. Such applications may require that the concentration of the electropositive organic additive be increased to compensate for the amount that is los through binding to host proteins. Lower operating conductivities in such circumstances may also enhance removal of DNA, endotoxin, and virus. In certain embodiments, the invention will generally support antibody recovery greater than 95%, and usually 98-99%. Conductivity and pH conditions of the sample should typically be established before adding either the ureide or the electropositive organic additive.

In certain embodiments, and contrary to most processes mediated by ionic interactions, it is recommended that evaluation of conditions to practice this invention specifically include and potentially favor conductivity values substantially above the practical minimum. Conditions significantly below physiological conductivity, especially when applied to crude samples such as cell culture supernatants, may encourage strong interactions of electropositive organic additive with acidic proteins, potentially producing at least two undesirable results, one being that such conditions may encourage the formation of precipitates. The other is that the sequestering of a subpopulation of the electropositive organic additives by acidic proteins and/or precipitates will reduce the available concentration of the remaining electropositive organic additive, with the potential effect of limiting the ability of the invention to reduce aggregate content. As a general matter, conductivity values up to 3 times physiological will support effective aggregate reduction, and antibody recovery greater than 90%.

In certain embodiments, and contrary to recommendations for most processes mediated by ionic interactions, especially between biomolecules and electropositive organic additives, pH may be reduced, even to values as low as 4 or below. Such extremes will be seldom if ever necessary, and may require higher conductivity to maintain protein solubility than neutral pH values.

In certain embodiments, one effective means of evaluating conditions for clarified cell culture supernatants containing IgG monoclonal antibodies is to cover a range of 0.005 to 0.05% electropositive organic additive, and conductivities ranging from physiological to 2 times physiological. The ranges can be extended further if desired, or narrowed. In the case that precipitation is observed within these ranges, it can frequently be prevented by increasing conductivity up to 3 times physiological without diminishing aggregate reduction. This corresponds to about 45 mS/cm. Higher conductivities may also serve. It will generally be advantageous to adjust the conductivity of a sample before adding the electropositive organic additive.

In certain embodiments, a convenient starting point for developing a purification procedure according to the invention for clarified cell culture supernatants is to use 0.02% ethacridine. Unclarified cell-containing harvests will likely benefit from the use of higher concentrations since the cells may bind sufficient electropositive organic additive to reduce the amount available for dissociation of heteroaggregates. A secondary benefit of the invention when applied to cell-containing preparations is that it substantially accelerates sedimentation of cells and debris, facilitating their removal. When the invention is applied to cell-containing preparations, it will be advisable to maintain near-physiological conditions to avoid excess cell mortality and/or expulsion of cell contents into the preparation.

In certain embodiments, it may be advantageous to begin by dispersing an organic modulator in the protein preparation before adding the electropositive organic additive, since that practice may improve antibody recovery. Long incubation before addition of the electropositive organic additive appears to be unnecessary; 15 minutes or less is adequate, although there appears to be no disadvantage to longer incubation. Experimental data generally indicate that addition of allantoin in a supersaturating amount of about 1% increases the recovery of IgG, when added in advance of the electropositive organic additive.

In certain embodiments, it is recommended that the electropositive organic additive cation be dissolved, for example in water or buffer, prior to its addition to the sample, to facilitate its rapid distribution throughout the protein preparation. Care should be taken to avoid persistent local excesses, for example by gradually infusing the dissolved electropositive organic additive into a well-mixing suspension. Incubation time should be at least 15 minutes, preferably 30, but appears not to benefit significantly from durations greater than 60 minutes.

The method may generally be practiced at ambient temperature but may be conducted at higher or lower temperatures, for example ranging from 4° to 37° C. Experimental data indicate that the temperature does not substantially alter the obtained results, which will leave the stability requirements of the protein the decisive factor in selection of operating temperature.

In certain embodiments, the electropositive organic additive is dissolved or dispersed, for example in water or buffer, and the pH adjusted prior to its addition to the sample. This is because certain electropositive organic additives, especially including cationic polymers, are extremely alkaline and have the potential to substantially altering the experimental conditions in an unintended manner.

In certain embodiments involving the use of both supersaturated ureides and electropositive organic additives, it may generally be advantageous to begin by dispersing the ureide in the protein preparation before adding the electropositive organic additive(s), since experience with the ureide allantoin indicates that this practice can improve antibody recovery. Long incubation before addition of the electropositive organic additive appears to be unnecessary; 15 minutes or less is adequate, although there appears to be no disadvantage to longer incubation.

In certain embodiments, it will be desirable to select an organic modulator and an electropositive organic additive to begin the process of determining which combination and operating conditions will be best suited to a particular application. The choice may be aided by the knowledge that the character of the electropositive organic additive at least partly determines the most suitable organic modulator, or working concentration of the organic modulator, and/or vice versa. In general terms, with respect to certain embodiments, the more hydrophobic the electropositive organic additive, the greater the requirement for an organic modulator with strong ability to weaken hydrophobic interactions, or a less hydrophobic modulator to be used at a higher concentration. This is oversimplified because modulation also involves hydrogen bonds, and different electropositive organic additive and different organic modulators can be expected to embody different balances of hydrophobic interactions and hydrogen bonding ability, but it illustrates the concept. Thus weakly-hydrophobic PEI may be preferred in some instances because it may give good results with a minimum concentration of a mild organic modulator, but PEI may be less preferred because of its known cytotoxic properties and the potential difficulties in detecting PEI with adequate sensitivity to easily validate its removal from the protein preparation through the course of a purification process. Strongly hydrophobic ethacridine might be less preferred in some instances because of its tendency to cause precipitation of materials with which it interacts, however, ethacridine may be preferred because of its long history in the field of plasma protein fractionation, and as an antiviral agent. In addition, its bright yellow color and intrinsic fluorescence facilitate sensitive measurement of its content in a given sample, thereby aiding documentation of its removal subsequent to practicing the method. Ethacridine's binding/precipitation tendencies can be compensated by an appropriate organic modulator at an appropriate concentration. The greater hydrophobicity of chlorhexidine will require a yet higher degree of modulation, but it choice may be discouraged by its strong UV absorbance at 280 nm.

Multiple options exist for monitoring the aggregate dissociation or removal achieved by the method, whether during method development or manufacturing. The simplest is to conduct analytical size exclusion chromatography on a column with suitable selectivity and monitor at a UV wavelength of 280 nm. This may reveal HMW (high molecular weight) aggregates, since they usually embody hydrodynamic dimension that reasonably conform to multiples of the size of the non-aggregated product. Hetero-aggregates are commonly overlooked by this method since their hydrodynamic dimensions may be only modestly greater than those of the non-aggregated product. In such cases, the heteromorphic composition of the aggregate may be revealed by calculating the ratio of UV absorbance at 254 (or 260) nm to absorbance at 280 nm, then comparing that value against the absorbance ratio for purified protein that is believed to be totally free of associated contaminants. Hetero-aggregates containing DNA, for example, will be revealed by an elevated ratio of 254/280. If the chromatograph offers the capability, ethacridine content can be monitored simultaneously at 365 nm. This can be helpful for documenting the removal of ethacridine through the subsequent purification process. Multiple wavelength monitoring can also be used in conjunction with other chromatography methods.

In certain embodiments, the invention can be integrated with treatment to remove the electropositive organic additive and potentially other components of the sample prior to subsequent purification. Such treatments may include exposure of the sample to solids bearing chemical moieties that are complementary in their nature to the characteristics of the electropositive organic additive(s), with the goal that they sequester the electropositive organic additive(s) from the remainder of the sample.

In certain embodiments, the invention can be integrated with one or more purification methods, including but not limited to protein A and other forms of biological affinity chromatography, anion exchange chromatography, cation exchange chromatography, hydrophobic interaction chromatography, immobilized metal affinity chromatography, hydroxyapatite or other mixed mode chromatography, and/or non-chromatographic methods such as precipitation and liquid-liquid extraction. It is within the purview of a person of ordinary skill in the art to develop appropriate conditions for the various methods and integrate them with the invention herein to achieve the necessary purification of a particular antibody.

In certain embodiments, it will be necessary to select at least one species of ureide for evaluation for use in practice of the invention. Uric acid is virtually insoluble, with the benefit that it is nearly absent from the treated protein preparation after removal of the undissolved uric acid, but dissolved allantoin appears to modulate the effects of electropositive organic additives, and typically supports higher antibody recovery. With respect to selection of electropositive organic additive, ethacridine offers several attractive features, particularly including its long history in the field of plasma protein fractionation, and as an antiviral agent. It also intercalates DNA and binds strongly to endotoxin. Additionally, its bright yellow color and intrinsic fluorescence facilitate sensitive measurement of its content in a given sample, thereby aiding documentation of its removal subsequent to practicing the method.

In certain embodiments, a desirable concentration of ureides and electropositive organic additive will be influenced by the composition of the protein preparation they are used to treat. A convenient starting point for clarified cell culture supernatants is 1% allantoin and 0.02% ethacridine. Both can be varied experimentally to fine-tune the amounts that provide the desired results. Application of the invention to cell-containing cell culture harvests will likely require larger amounts of both ureide and electropositive organic additive. Experimental data particularly indicate that in certain embodiments a higher amount of allantoin may be required to achieve supersaturation, and a higher amount of ethacridine may be required to compensate for the amount lost on cell surfaces. Experimentation may help identify the suitably effective amounts of both. The invention provides in certain embodiments the valuable benefit of increasing antibody recovery by dissociating rather than removing aggregates, especially in situations where very high cell density cultures produce large proportions of aggregated antibody. This in turn may enable the purification of proteins from extremely high-producing cell cultures, with the result of substantially improving the productivity and economy of the production/purification process overall. Another benefit of the invention is that it substantially accelerates sedimentation of cells and debris, facilitating their removal.

Data from differential scanning calorimetry indicate that 35 mM (near-saturated) allantoin has the effect of lowering thermal transition temperatures for IgG by about half the amount to which 35 mM urea lowers thermal transition temperatures. This indicates that the risk of protein denaturation with allantoin is nil. It also indicates that the combination of allantoin with an electropositive organic additive may increase viral inactivation levels over those achieved with electropositive organic additive alone where such viral inactivation appears to occur in addition to the binding of virus by undissolved ureides.

EXAMPLES

Example 1

Comparison of electropositive organic additives for reduction of HMW aggregates and dissociation of hetero-aggregates. Monoclonal IgM-containing clarified cell culture supernatant was analyzed by size exclusion chromatography conducted in a buffer of 200 mM arginine, 10 mM EDTA, 50 mM MES, pH 6.5. The material contained 11% HMW aggregates and the IgM peak exhibited a 254/280 ratio of 0.506 indicating a substantial presence of hetero-aggregates. Conductivity of the supernatant was raised to 20 mS/cm by addition of sodium chloride. 9 samples were treated with 0.01, 0.05, and 0.1% PEI-1200, 0.01, 0.05, and 0.1% ethacridine, and 0.01, 0.05, and 0.1% chlorhexidine, incubated for 30 minutes then analyzed by SEC (results below). The 0.1% chlorhexidine sample precipitated before analysis. The samples were incubated for 30 minutes then analyzed by SEC. Only ethacridine eliminated HMW aggregates. It also supported effective hetero-aggregate dissociation. PEI offered greater than 97% recovery at all concentrations, and good hetero-aggregate dissociation, but poor reduction of heteroaggregates. Chlorhexidine was roughly intermediate between ethacridine and PEI.

| Sample | % Recovery | HMW aggregates | Hetero-aggregates |
| --- | --- | --- | --- |
| A6 OM | 100 | 11.14 | 0.506 |
| A6 PEI 0.01 | 99.56 | 7.16 | 0.466 |
| A6 PEI 0.05 | 97.65 | 4.56 | 0.466 |
| A6 PEI 0.10 | 97.05 | 4.37 | 0.459 |
| A6 Eth 0.01 | 95.67 | 6.7 | 0.473 |
| A6 Eth 0.05 | 88.18 | 0 | 0.458 |
| A6 Eth 0.10 | 66.36 | 0 | 0.473 |
| A6 Ch 0.01 | 93.93 | 0.38 | 0.440 |
| A6 Ch 0.05 | 86.23 | 3.35 | 0.461 |

Example 2

Comparison of electropositive organic additives for reduction of HMW aggregates and dissociation of hetero-aggregates. The form of Example 1 was repeated with anther antibody. This antibody exhibited 7.5% HMW aggregates and a lower hetero-aggregate content. Trends were basically the same as in Example 1, but with clear differences, apparently attributable to the characteristics of the antibody. See below.

| Sample | % Recovery | HMW aggregates | 254/280 |
| --- | --- | --- | --- |
| M84 OM | 100 | 7.49 | 0.482 |
| M84 PEI 0.01 | 99.59 | 5.18 | 0.463 |
| M84 PEI 0.05 | 99.59 | 2.69 | 0.462 |
| M84 PEI 0.10 | 96.86 | 0 | 0.456 |
| M84 Eth 0.01 | 99.47 | 4.97 | 0.461 |
| M84 Eth 0.05 | 96.05 | 0 | 0.454 |
| M84 Eth 0.10 | 109.63 | 0 | 0.458 |
| M84 Ch 0.01 | 86.50 | 0 | 0.439 |
| M84 Ch 0.05 | 81.38 | 0 | 0.456 |

Example 3

The effect of higher conductivity. The ethacridine series of Example 2 was repeated at a supernatant conductivity of 40 mS/cm. HMW aggregate and hetero-aggregate levels were lower in the untreated control than at 20 mS/cm. HMW aggregates trended the same way versus ethacridine concentration, but heteroaggregates trended in the opposite direction, while recoveries were lower.

| Sample | % Recovery | HMW aggregates | 254/280 |
| --- | --- | --- | --- |
| M84 OM | 100 | 4.21 | 0.473 |
| M84 Eth 0.01 | 98.18 | 1.86 | 0.453 |
| M84 Eth 0.05 | 58.91 | 0 | 0.469 |
| M84 Eth 0.10 | 57.52 | 0 | 0.486 |

Example 4

Determination of working concentrations for reducing the level of DNA-antibody hetero-aggregates in a monoclonal IgM-containing cell-culture supernatant. Hydroxyapatite chromatography showed that monoclonal IgM clone 85 was heavily complexed with DNA. This was revealed by the UV absorbance of the IgM peak at 254 nm being roughly equivalent to its UV absorbance at 280 nm. DNA-free IgM has a 280/254 ratio of about 2:1. An experiment was set up whereby 10 mL samples of monoclonal IgM-containing clarified cell culture supernatant were combined with varying combinations of the electropositive organic additive PEI-1300 and the ureide allantoin to determine the most effective combination for dissociating DNA from IgM. The samples were initially tan in color due to the presence of contaminants, and lightly turbid, indicating the presence of precipitates. All samples were saturated with allantoin by direct addition of dry allantoin powder. All allantoin-containing samples were densely milky in appearance. A stock solution of PEI was prepared by titrating 50% PEI-1300 (Sigma) to pH 7.0 with acetic acid and adding water to a final PEI concentration of 10%. PEI was added to samples to yield final concentrations of 2%, 1%, 0.5%, 0.025%, 0.0125%, and 0.00625%. An experimental control was prepared, lacking PEI but including allantoin. Another control was prepared with 0.05% PEI in the absence of allantoin. Turbidity remained unchanged in the latter control, indicating the inability of the PEI-1300 alone to cause substantial precipitation of DNA or other sample components. Each sample was filtered through a 0.22 µm membrane. Samples filtered easily and were sparkling optically clear after treatment. This is a particular feature of the invention. Each sample was applied to a column of hydroxyapatite (CHT type II, 40 µm, 1 mL, 5×50 mm, 1 mL/min) equilibrated with 50 mM Hepes, pH 7.0; washed with 50 mM Hepes, 2 M NaCl, pH 7.0; re-equilibrated to initial conditions; eluted with a 10 column volume (CV) linear gradient to 250 mM sodium phosphate, pH 7.0; then cleaned with 500 mM phosphate, pH 7.0. The PEI-only sample showed partial dissociation. A very large DNA peak eluted in the cleaning step. The allantoin-only sample showed less reduction of complexed DNA, but very little DNA eluted in the cleaning peak. IgM eluted from all of the PEI/allantoin-treated samples gave the ideal 280/254 ratio indicating essentially complete DNA dissociation from the IgM, with only a negligible amount of DNA eluting in the cleaning step. Hydroxyapatite-fractionated IgM collected from the experiment at 1% PEI was applied to an analytical SEC column. The IgM was estimated to be greater than 95% pure with no indication of remaining DNA. This example illustrates the ability of the invention to enable effective product capture by a method normally rendered ineffective by the presence of high DNA levels in the feed. It also reveals that the combination of a electropositive organic additive and a hydrogen donor/acceptor can achieve fine distinctions between DNA—which has a high affinity for electropositive organic additives—and products with high but lower-than-DNA affinities for electropositive organic additives. This experiment also yielded an important insight and example of the value of this technology. The DNA peak on the PEI-only treatment was roughly twice as large as the DNA peak on the untreated sample. This shows that roughly half of the DNA in the original sample was contained in hetero-aggregates with proteins, and highlights the importance of their dissociation. This example also highlights the ability of the method to achieve the highly unusual and desirable results of achieving crystal-clear biological samples. Many methods exist for clarification of cell culture supernatants but all leave a distinct haziness in the sample, and this haziness is often suspected of interfering with subsequent methods for purification. The dramatic clarity of solutions treated with the method, especially when conducted in conjunction with undissolved allantoin, emphasizes its distinctness from other methods.

Example 5

Determination of preferred sequence of addition. An experiment was conducted in which two aliquots of the antibody described in Example 4 were treated with 0.025% PEI-1300 and saturated allantoin. PEI was added first in one experiment, allantoin first in the other. The samples were filtered and applied to a hydroxyapatite column as described above. The IgM peak from the allantoin-first treatment was roughly twice as large as the peak from the PEI-first treatment. These results highlight the importance of order of addition to maximize product recovery, and also emphasize the ability of allantoin to modulate the interaction of electropositive organic additives with proteins.

Example 6

Determination of incubation time. Experiments were conducted in which the allantoin was allowed to incubate for intervals ranging from 1 to 30 minutes before PEI addition, and 1-30 minutes following PEI addition, before filtration. No trends were apparent in the 280/254 ratio or size of the IgM peak on the hydroxyapatite column. This suggests that the kinetics of DNA dissociation and removal are rapid.

Example 7

Purification of IgM by steric exclusion chromatography on a monolith. A sample of IgM-B07 cell culture supernatant was treated with 1% PEI-1200 and saturated allantoin as described above. An 8 mL hydroxyl monolith (BIA Separations) was equilibrated with 50 mM Hepes, 100 mM NaCl, 10 mM EDTA, 10% polyethylene glycol-6000, pH 7.0. Treated IgM supernatant was applied at 10% PEG; the column was washed with equilibration buffer, then eluted with a 3.75 CV linear gradient to 50 mM Hepes, 100 mM NaCl, pH 7.0. An untreated sample was subsequently chromatographed for reference. The untreated reference sample eluted in a broad, trailing, dilute, turbid peak. The treated sample eluted in a sharp, symmetrical, concentrated, optically clear peak, well resolved from a trailing peak of aggregates. Analytical SEC showed IgM from the treated sample to be greater than 95% pure and aggregate-free after only this single chromatography step.

Example 8

DNA removal of enzymatically digested DNA. Monoclonal IgM clone A4 was treated in advance with benzonase to digest the DNA into fragments. It was then treated with saturated allantoin and 0.01% PEI-1300 to dissociate hetero-aggregates. The precipitate was removed and the sample fractionated by steric exclusion chromatography. DNA was essentially absent from the eluted antibody, indicating that the effectiveness of the invention for removal of small DNA fragments is equivalent to its effectiveness for removing large DNA.

Example 9

The form of Example 4 was repeated but with ethacridine in place of PEI-1300. It was found that ethacridine produced similar results but offered a narrower dynamic range. Antibody recovery was inversely proportional to ethacridine concentration down to 0.00625%. The efficiency of DNA dissociation was proportional to ethacridine concentration from 0.001% to 0.00625%.

Example 10

Dissociation of IgM-DNA complexes with chlorhexidine. Filtered cell culture supernatant containing IgM 85 was applied to a strong anion exchange porous particle resin (EMD TMAE) and fractionated in a linear gradient to 1 M NaCl (pH 7.0). Despite known high DNA content, the DNA peak appeared to represent about 2% of the total DNA. Peaks with elevated absorption at 254 nm, eluting between IgM and DNA, showed that the rest of the DNA was resident in hetero-aggregates. A sample of IgM 85 treated with saturated allantoin, showed a small but definite reduction in the amount of hetero-aggregates and a corresponding increase in the DNA peak. Chlorhexidine was added to allantoin-saturated samples, at levels ranging from 0.001 to 1%, and the treated samples applied to the anion exchanger. Hetero-aggregates were dissociated and DNA eliminated in the range of 0.01-1.0% chlorhexidine. Complexes were only partially dissociated at lower concentrations, and DNA reduction was minimal. Severe antibody losses were observed at 1% and 0.5% chlorhexidine. These results show that while chlorhexidine is effective for hetero-aggregate dissociation and DNA removal in the presence of saturated allantoin, its effective range is both higher and narrower than PEI-1300 or ethacridine. This example also illustrates the enablement of anion exchange chromatography as an IgM capture method by virtue of the invention having removed DNA in advance. Compare with Example 4, which demonstrated enablement of hydroxyapatite as an IgM capture method.

Example 11

As revealed by the above experiments, increasing hydrophobicity of the electropositive organic additive, for example in the series of PEI, ethacridine, chlorhexidine, results in a narrowing of the useful dynamic range, and an increasing loss of the protein of interest. An experimental comparison was made between 1% uric and 1% allantoin in combination with 0.02% ethacridine or 0.02% PEI-1300. IgM recovery was equivalent for PEI with both ureides, and for ethacridine with allantoin, but reduced to about 94% with the combination of uric acid with ethacridine. These results were interpreted to indicate that the saturated component allantoin (about 36 mM) in the undissolved solution, modified the interaction of ethacridine with the antibody. Dissociation of aggregates was equivalent among all treatments. SEC also revealed, as in all above experiments, that the apparent size of the antibody peak was reduced as a result of treatment. This was observed as a slight but definite increase in elution time, clearly revealed by overlaying the profiles. Parallel reduction of 254/280 ratio indicated that the change in size was due to removal of 254-dominant contaminants associated with the antibody.

Example 12

Addition of allantoin and ethacridine to cell-containing culture broth. 1.5 L of hybridoma culture broth was harvested from shake flasks. The conductivity was adjusted to 25 mS/cm and allantoin and ethacridine were added to the broth to 1% (w/v) and 0.02% (w/v) respectively and mixed well for 20 minutes at room temperature. The mixture was clarified by centrifugation and analyzed by analytical SEC. At this early stage, no hetero-aggregates were observed and the 254/280 peak height ratio of the IgM peak was 1:2, showing that the IgM was largely free of DNA contaminants. This example shows that it is possible to integrate the removal of DNA and dissociation of aggregates with cell removal.

Example 13

Determination of working concentrations for reducing the level of DNA-antibody hetero-aggregates in a monoclonal IgM-containing cell-culture supernatant. Hydroxyapatite chromatography showed that monoclonal IgM clone 85 was heavily complexed with DNA. This was revealed by the UV absorbance of the IgM peak at 254 nm being roughly equivalent to its UV absorbance at 280 nm. DNA-free IgM has a 280/254 ratio of about 2:1. An experiment was set up whereby 10 mL samples of monoclonal IgM-containing clarified cell culture supernatant were combined with varying combinations of the electropositive organic additive PEI-1300 and 1 M urea to determine the most effective combination for dissociating DNA from IgM. The samples were initially tan in color due to the presence of contaminants, and lightly turbid, indicating the presence of precipitates. A stock solution of PEI was prepared by titrating 50% PEI-1300 (Sigma) to pH 7.0 with acetic acid and adding water to a final PEI concentration of 10%. PEI was added to samples to yield final concentrations of 2%, 1%, 0.5%, 0.025%, 0.0125%, and 0.00625%. Dry urea was added to a concentration of 1 M. An experimental control was prepared, lacking PEI but including 1 M urea. Another control was prepared with 0.05% PEI absent urea. Turbidity remained unchanged in the latter control. Each sample was filtered through a 0.22 µm membrane. Each sample was applied to a column of hydroxyapatite (CHT type II, 40 µm, 1 mL, 5×50 mm, 1 mL/min) equilibrated with 50 mM Hepes, pH 7.0; washed with 50 mM Hepes, 2 M NaCl, pH 7.0; re-equilibrated to initial conditions; eluted with a 10 column volume (CV) linear gradient to 250 mM sodium phosphate, pH 7.0; then cleaned with 500 mM phosphate, pH 7.0. The PEI-only sample showed partial dissociation of hetero-aggregates, but very large DNA peak in the cleaning step showed that hetero-aggregate dissociation was nevertheless substantial. The urea-only sample showed less reduction of hetero-aggregates, and less DNA in the cleaning peak. IgM eluted from all of the PEI/urea-treated samples gave 280/254 ratio of greater than 2.0 indicating essentially complete hetero-aggregate dissociation, with only a negligible amount of DNA eluting in the cleaning step. Hydroxyapatite-fractionated IgM collected from the experiment at 1% PEI was applied to an analytical SEC column. The IgM was estimated to be greater than 95% pure with less than 0.2% HMW aggregate and no apparent hetero-aggregates. Recovery was 98-99%. This example illustrates the ability of the invention to enable effective product capture by a method normally rendered ineffective by the presence of high DNA levels in the feed. These results, compared to the untreated sample highlight the important point that most of the DNA in the original sample was involved in hetero-aggregates, with the antibody and with other proteins.

Example 14

Determination of preferred sequence of addition. An experiment was conducted in which two aliquots of the antibody described in Example 14 were treated with 0.025% PEI-1300 and 1 M urea. PEI was added first in one experiment, urea first in the other. The samples were filtered and applied to a hydroxyapatite column as described above. The IgM peak from the urea-first treatment was roughly twice as large as the peak from the PEI-first treatment. These results highlight the importance of order of addition to maximize product recovery, and also emphasize the ability of urea to modulate the interaction of electropositive organic additives with proteins.

Example 15

Purification of decomplexed IgM by steric exclusion chromatography on a monolith. A sample of IgM-B07 cell culture supernatant was treated with 1% PEI-1200 and 10% propylene glycol. An 8 mL hydroxyl monolith (BIA Separations) was equilibrated with 50 mM Hepes, 100 mM NaCl, 10 mM EDTA, 10% polyethylene glycol-6000, pH 7.0. Treated IgM supernatant was applied at 10% PEG; the column was washed with equilibration buffer, then eluted with a 3.75 CV linear gradient to 50 mM Hepes, 100 mM NaCl, pH 7.0. An untreated sample was subsequently chromatographed for reference. The untreated reference sample eluted in a broad, trailing, dilute, turbid peak. The treated sample eluted in a sharp, symmetrical, concentrated, optically clear peak. Analytical SEC showed IgM from the treated sample to be greater than 95% pure, with less than 0.1% HMW aggregates and no apparent hetero-aggregates.

Example 16

Dissociation of IgM hetero-aggregates with chlorhexidine. Filtered cell culture supernatant containing IgM 85 was applied to a strong anion exchange porous particle resin (EMD TMAE) and fractionated in a linear gradient to 1 M NaCl (pH 7.0). Despite known high DNA content, the DNA peak appeared to represent only about 2% of the total DNA. Peaks with elevated absorption at 254 nm, eluting between IgM and DNA, showed that the rest of the DNA was resident in hetero-aggregates. A sample of IgM 85 treated with 1 M urea (no chlorhexidine), showed a small but definite reduction in the amount of hetero-aggregates and a corresponding increase in the DNA peak. Chlorhexidine was added to 1 M urea samples, at levels ranging from 0.001% to 1%, and the treated samples applied to the anion exchanger. Hetero-aggregates were dissociated and DNA eliminated in the range of 0.01-1.0% chlorhexidine. Hetero-aggregates were only partially dissociated at lower concentrations, and DNA reduction was minimal. Severe antibody losses were observed at 0.5% and 1% chlorhexidine. These results show that while chlorhexidine is effective for removal of HMW aggregates and dissociation of hetero-aggregates, its effective range is both higher and narrower than PEI-1300 or ethacridine. This example also illustrates the enablement of anion exchange chromatography as an IgM capture method by virtue of the invention having removed DNA in advance. Compare with Example 14, which demonstrated enablement of hydroxyapatite as an IgM capture method.

Example 17

Virus and DNA reduction. Cell cultures containing live samples of murine leukemia virus (MuLV), minute virus of mice (MVM), and Chinese hamster ovary (CHO) cells were treated with 1% allantoin and 0.025% ethacridine. All experiments were conducted at physiological conditions. MuLV was reduced by 1.6 log. MVM was reduced by 3.1 log. DNA in the CHO culture was reduced by 2.1 log. A parallel series of samples treated with 0.025% ethacridine in the absence of allantoin was less effective, reducing MuLV by 1.3 logs, MVM by 1.4 logs, and DNA by 1.6 logs.

It will be understood by the person of ordinary skill in the art how to scale up or scale down the results from experiments such as those described in the above examples, to whatever volume required to meet their particular requirements.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of reducing the aggregate content of a sample, wherein the sample comprises a target antibody and aggregates comprising nucleic acid contaminants associated with the target antibody, the method comprising:
   (a) contacting the sample with an electropositive organic additive at a non-zero amount of 0.1% weight/volume or less, and an undissolved allantoin, thereby forming a mixture comprising allantoin and precipitated nucleic acid contaminants, wherein allantoin is supersaturated in the mixture and the electropositive organic additive comprises ethacridine or polyethyleneimine; and
   (b) removing the undissolved allantoin and precipitated nucleic acid contaminants from the sample,
   wherein the sample, after (b) comprises the target antibody and a reduced amount of the aggregates, wherein the sample is derived from a cell culture or cell culture supernatant, and the target antibody is a recombinant antibody.

2. A method of reducing the aggregate content of a sample, wherein the sample comprises a target antibody and aggregates comprising nucleic acid contaminants associated with the target antibody, the method comprising:
   (a) contacting the sample having a conductivity value of 5 mS/cm or higher with an electropositive organic additive at a non-zero amount of 0.1% weight/volume or less, and an undissolved allantoin, thereby forming a mixture comprising allantoin and precipitated nucleic acid contaminants, wherein allantoin is supersaturated in the mixture and the electropositive organic additive comprises ethacridine or polyethyleneimine; and
   (b) removing the undissolved allantoin and precipitated nucleic acid contaminants from the sample,
   wherein the sample, after (b) comprises the target antibody and a reduced amount of the aggregates, wherein the sample is derived from a cell culture or cell culture supernatant, and the target antibody is a recombinant antibody.

3. The method of claim 1 or 2, wherein allantoin is present in the mixture in a range of from about 0.5% to about 2% weight/volume.

4. The method of claim 1 or 2, wherein the undissolved allantoin is added to the sample before the electropositive organic additive.

5. The method of claim 2, wherein the antibody comprises an antibody fragment.

6. The method of claim 1 or 2, wherein the amount of the electropositive organic additive in the mixture is 0.01% or less weight/volume.

7. The method of claim 1 or 2, wherein the amount of the electropositive organic additive in the mixture is 0.001% or less weight/volume.

8. The method of claim 1 or 2, wherein the amount of the electropositive organic additive in the mixture is from 0.02% to 0.03%.

9. The method of claim 1, wherein two or more electropositive organic additives are present in the mixture.

10. The method of claim 9, wherein the total concentration of the two or more electropositive organic additives in the mixture is 0.1% or less weight/volume.

11. The method of claim 10, wherein the total concentration of the two or more electropositive organic additives in the mixture is 0.01% or less weight/volume.

12. The method of claim 11, wherein the total concentration of the two or more electropositive organic additives in the mixture is 0.001% or less weight/volume.

13. The method of claim 3, wherein allantoin is present in the mixture at a concentration in range of from about 0.56% weight/volume to about 1% weight/volume.

14. The method of claim 3, wherein allantoin is present in the mixture at a concentration in range of from about 1% weight/volume to about 2% weight/volume.

15. The method of claim 1 or 2, wherein allantoin is present at a concentration in range of from about 2% weight/volume to about 5% weight/volume.

16. The method of claim 1 or 2, wherein allantoin is present in the mixture at a concentration in range of from about 5% weight/volume to about 10% weight/volume.

17. The method of claim 1 or 2, wherein allantoin is present in the mixture at a concentration in range of from about 10% weight/volume to about 15% weight/volume.

18. The method of claim 2, wherein the conductivity of the sample is adjusted to a level that is higher than necessary to counteract substantial loss of the antibody.

19. The method of claim 2, wherein the conductivity of the sample is adjusted to greater than 20 mS/cm.

20. The method of claim 2, wherein the conductivity of the sample is adjusted up to greater than 25 mS/cm.

21. The method of claim 18, wherein the conductivity of the sample is adjusted before addition of the electropositive organic additive.

22. The method of claim 1, wherein the sample comprises polyethylene glycol or wherein polyethylene glycol is added to the sample.

23. The method of claim 22, wherein the polyethylene glycol is at, or is added to a concentration in a range of from about 0.01% to about 20% weight/volume.

24. The method of claim 22, wherein the polyethylene glycol is at, or is added to a concentration in range of from about 0.01 to about 1%.

25. The method of claim 22, wherein the polyethylene glycol is at, or is added to a concentration in range of from about 1% to about 5%.

26. The method of claim 22, wherein the polyethylene glycol is at, or is added to a concentration in range of from about 5% to about 10%.

27. The method of claim 22, wherein the polyethylene glycol is at, or is added to a concentration in range of from about 10% to about 20%.

28. The method of claim 1, wherein a surfactant is present in the mixture.

29. The method of claim 28, wherein the surfactant comprises a nonionic surfactant.

30. The method of claim 29, wherein the nonionic surfactant comprises one selected from the group consisting of Tween and Triton.

31. The method of claim 28, wherein the surfactant comprises a zwitterionic surfactant.

32. The method of claim 31, wherein the zwitterionic surfactant comprises one selected from the group consisting of CHAPS, CHAPSO, and octaglucoside.

33. The method of claim 28, wherein the surfactant is present in the mixture at a non-zero concentration less than 1%.

34. The method of claim 28, wherein the surfactant is present in the mixture at a non-zero concentration less than 0.1%.

35. The method of claim 28, wherein the surfactant is present in the mixture at a non-zero concentration less than 0.01%.

36. The method of claim 1, wherein a chelating agent is present in the mixture.

37. The method of claim 36, wherein the chelating agent is positively charged.

38. The method of claim 37, wherein the positively charged chelating agent comprises tris(2-aminoethyl)amine or deferoxamine.

39. The method of claim 36, wherein the chelating agent is present in the mixture at a non-zero concentration of less than 100 mM.

40. The method of claim 36, wherein the chelating agent is present in the mixture at a non-zero concentration of less than 50 mM.

41. The method of claim 36, wherein the chelating agent is present in the mixture at a non-zero concentration of less than 20 mM.

42. The method of claim 36, wherein the chelating agent is present in the mixture at a non-zero concentration of less than 10 mM.

43. The method of claim 36, wherein the chelating agent is present in the mixture at a non-zero concentration of less than 5 mM.

44. The method of claim 1, wherein the contacting of the sample with the undissolved allantoin comprises contacting the sample with allantoin in an amount of greater than 0.5% (w/v).

* * * * *